United States Patent
Mostafavi

(10) Patent No.: US 9,773,318 B2
(45) Date of Patent: Sep. 26, 2017

(54) SYSTEMS AND METHODS FOR DETECTING CAMERA DEFECT CAUSED BY EXPOSURE TO RADIATION

(71) Applicant: Varian Medical Systems, Inc., Palo Alto, CA (US)

(72) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 14/874,070

(22) Filed: Oct. 2, 2015

(65) Prior Publication Data

US 2017/0098308 A1 Apr. 6, 2017

(51) Int. Cl.
| | | |
|---|---|---|
| G06K 9/34 | (2006.01) | |
| G06K 9/40 | (2006.01) | |
| G06T 7/00 | (2017.01) | |
| G06T 5/00 | (2006.01) | |
| A61F 2/30 | (2006.01) | |

(52) U.S. Cl.
CPC ........ *G06T 7/0081* (2013.01); *A61F 2/30942* (2013.01); *G06T 5/002* (2013.01); *G06T 7/0012* (2013.01); *G06T 7/0087* (2013.01); *G06T 2207/10081* (2013.01); *G06T 2207/10088* (2013.01); *G06T 2207/20148* (2013.01); *G06T 2210/41* (2013.01)

(58) Field of Classification Search
CPC . G06T 2207/10116; G06T 2207/10132; G06T 2207/30172; G06T 7/0028; G06T 7/0012; G06T 7/0081; G06T 2207/10088; G06T 2207/10072; G06T 2207/20148; G06T 2207/10081; G06T 2210/41; G06T 5/002; G06T 7/0087; A61F 2/30942
USPC .................................................. 382/173, 275
See application file for complete search history.

(56) References Cited

U.S. PATENT DOCUMENTS

| | | | | |
|---|---|---|---|---|
| 8,560,329 B2 * | 10/2013 | Qi | ........................... | G10L 19/06 704/217 |
| 2010/0121584 A1 * | 5/2010 | Moreau | ................ | G01N 29/043 702/56 |
| 2012/0130243 A1 * | 5/2012 | Balocco | ............... | A61B 8/0891 600/443 |
| 2015/0063541 A1 * | 3/2015 | Kobayashi | ............... | A61B 6/12 378/62 |
| 2015/0110403 A1 * | 4/2015 | Cho | ........................ | G06T 5/003 382/195 |

* cited by examiner

*Primary Examiner* — Kanjibhai Patel
(74) *Attorney, Agent, or Firm* — Vista IP Law Group, LLP

(57) ABSTRACT

A method of detecting camera defect includes: obtaining an image by a processing unit, the processing unit having a surface fit module, a subtraction module, and a peak quantification module; determining a first autocorrelation map for a first sub-region in the image; determining, using the surface fit module, a first surface fit for first scene content in the first sub-region; subtracting, using the subtraction module, the first surface fit from the first autocorrelation map for the first sub-region in the image to obtain a first residual map; and quantifying, using the peak quantification module, a first noise in the first residual map.

29 Claims, 9 Drawing Sheets
(6 of 9 Drawing Sheet(s) Filed in Color)

SYSTEMS AND METHODS FOR DETECTING CAMERA DEFECT CAUSED BY EXPOSURE TO RADIATION

FIELD

The field of the application relates to cameras for use in medical procedures, and more particularly, to systems and methods for detecting camera defect caused by exposure to radiation.

BACKGROUND

Radiation therapy involves medical procedures that selectively expose certain areas of a human body, such as cancerous tumors, to high doses of radiation. Radiation may also be used to obtain images of the patient during an imaging procedure.

In some medical procedures involving use of radiation, one or more cameras may be set up to perform one or more functions during the medical procedures. For example, a camera may be used to monitor a position of a patient as the patient is being treated by radiation. The camera may also be used to determine a breathing phase of a patient as the patient is being treated by treatment radiation, and/or imaged by diagnostic radiation. In some cases, one or more cameras may be used to detect possible collision between a treatment machine and the patient.

Camera used with radiation procedure is exposed to radiation, which can damage the camera gradually over time.

In accordance with one or more embodiments described herein, a quantitative measure of the camera defect and an automatic image analysis method that generates this quantitative measure from camera images (e.g., those from a live video stream) are provided. Such technique is advantageous because the measure may be obtained without requiring a user to run regularly scheduled tests for the camera.

SUMMARY

A method of detecting camera defect includes: obtaining an image by a processing unit, the processing unit having a surface fit module, a subtraction module, and a peak quantification module; determining a first autocorrelation map for a first sub-region in the image; determining, using the surface fit module, a first surface fit for first scene content in the first sub-region; subtracting, using the subtraction module, the first surface fit from the first autocorrelation map for the first sub-region in the image to obtain a first residual map; and quantifying, using the peak quantification module, a first noise in the first residual map.

Optionally, the act of determining the surface fit comprises determining a planar surface that represents the first scene content.

Optionally, the act of determining the surface fit comprises determining a non-planar surface that represents the first scene content.

Optionally, the act of quantifying the first noise comprises determining whether a magnitude of the first noise exceeds a threshold or not.

Optionally, the method further includes determining a level of confidence associated with the quantified first noise.

Optionally, the act of determining the level of confidence comprises determining a standard deviation associated with a residual sidelobe in the first residual map.

Optionally, the method further includes displaying the image in a screen, and displaying an indicator representing the quantified first noise in the screen.

Optionally, the indicator has a first color if the quantified first noise is above a threshold, and a second color if the quantified first noise is below the threshold.

Optionally, the indicator has a first color if the quantified first noise is above a threshold, and the quantified first noise is determined with confidence, the indicator has a second color if the quantified first noise is below the threshold, and the quantified first noise is determined with confidence, and the indicator has a third color if the quantified first noise cannot be determined with confidence.

Optionally, the indicator is displayed over the image, and is at a location that corresponds with a position of the sub-region in the image.

Optionally, the indicator comprises a dot.

Optionally, the method further includes determining a second autocorrelation map for a second sub-region in the image; determining a second surface fit for second scene content in the second sub-region; subtracting the second surface fit from the second autocorrelation map for the second sub-region in the image to obtain a second residual map; and quantifying a second noise in the second residual map.

Optionally, the method further includes: obtaining an additional image; determining a second autocorrelation map for a second sub-region in the additional image; determining a second surface fit for second scene content in the second sub-region; subtracting the second surface fit from the second autocorrelation map for the second sub-region in the image to obtain a second residual map; and quantifying a second noise in the second residual map; wherein the first image and the additional image are obtained at different respective times; and wherein a position of the first sub-region with respect to the image is a same as a position of the second sub-region with respect to the additional image. Optionally the method is applied to a time average of an image sequence. Time averaging may be recursive or block (boxcar) average.

Optionally, the method further includes presenting the quantified first noise and the quantified second noise as a function of time.

An apparatus for detecting camera defect includes: a processing unit having a surface fit module, a subtraction module, and a peak quantification module; wherein the processing unit is configured to obtain an image, and determining a first autocorrelation map for a first sub-region in the image; wherein the surface fit module is configured to determine a first surface fit for first scene content in the first sub-region; wherein the subtraction module is configured to subtract the first surface fit from the first autocorrelation map for the first sub-region in the image to obtain a first residual map; and wherein the peak quantification module is configured to quantify a first noise in the first residual map.

Optionally, the surface fit module is configured to determine the surface fit by determining a planar surface that represents the first scene content.

Optionally, the surface fit module is configured to determine the surface fit by determining a non-planar surface that represents the first scene content.

Optionally, the peak quantification module is configured to quantify the first noise by determining whether a magnitude of the first noise exceeds a threshold or not.

Optionally, the apparatus further includes a confidence level module configured to determine a level of confidence associated with the quantified first noise.

Optionally, the confidence level module is configured to determine the level of confidence by determining a standard deviation associated with a residual sidelobe in the first residual map.

Optionally, the apparatus further includes a screen for displaying the image, and for displaying an indicator representing the quantified first noise.

Optionally, the indicator has a first color if the quantified first noise is above a threshold, and a second color if the quantified first noise is below the threshold.

Optionally, the indicator has a first color if the quantified first noise is above a threshold, and the quantified first noise is determined with confidence, the indicator has a second color if the quantified first noise is below the threshold, and the quantified first noise is determined with confidence, and the indicator has a third color if the quantified first noise cannot be determined with confidence.

Optionally, the screen is configured to display the indicator over the image at a location that corresponds with a position of the sub-region in the image.

Optionally, the indicator comprises a dot.

Optionally, the processing unit is configured to determine a second autocorrelation map for a second sub-region in the image; wherein the surface fit module is configured to determine a second surface fit for second scene content in the second sub-region; wherein the subtraction module is configured to subtract the second surface fit from the second autocorrelation map for the second sub-region in the image to obtain a second residual map; and wherein the peak quantification module is configured to quantify a second noise in the second residual map.

Optionally, the processing unit is configured to obtain an additional image, and determine a second autocorrelation map for a second sub-region in the additional image; wherein the surface module is configured to determine a second surface fit for second scene content in the second sub-region; wherein the subtraction module is configured to subtract the second surface fit from the second autocorrelation map for the second sub-region in the image to obtain a second residual map; and wherein the peak quantification module is configured to quantify a second noise in the second residual map; wherein the first image and the additional image are obtained at different respective times; and wherein a position of the first sub-region with respect to the image is a same as a position of the second sub-region with respect to the additional image.

Optionally, the apparatus further includes a screen for presenting the quantified first noise and the quantified second noise as a function of time.

A processor-program product includes a set of instruction, an execution of which by a processing unit causes a method of detecting camera defect to be performed, the method comprising: obtaining an image; determining a first autocorrelation map for a first sub-region in the image; determining, using a surface fit module, a first surface fit for first scene content in the first sub-region; subtracting, using a subtraction module, the first surface fit from the first autocorrelation map for the first sub-region in the image to obtain a first residual map; and quantifying, using a peak quantification module, a first noise in the first residual map.

Other and further aspects and features will be evident from reading the following detailed description.

DESCRIPTION OF THE DRAWINGS

The patent or application file contains at least one drawing executed in color. Copies of this patent or patent application publication with color drawing(s) will be provided by the Office upon request and payment of the necessary fee.

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
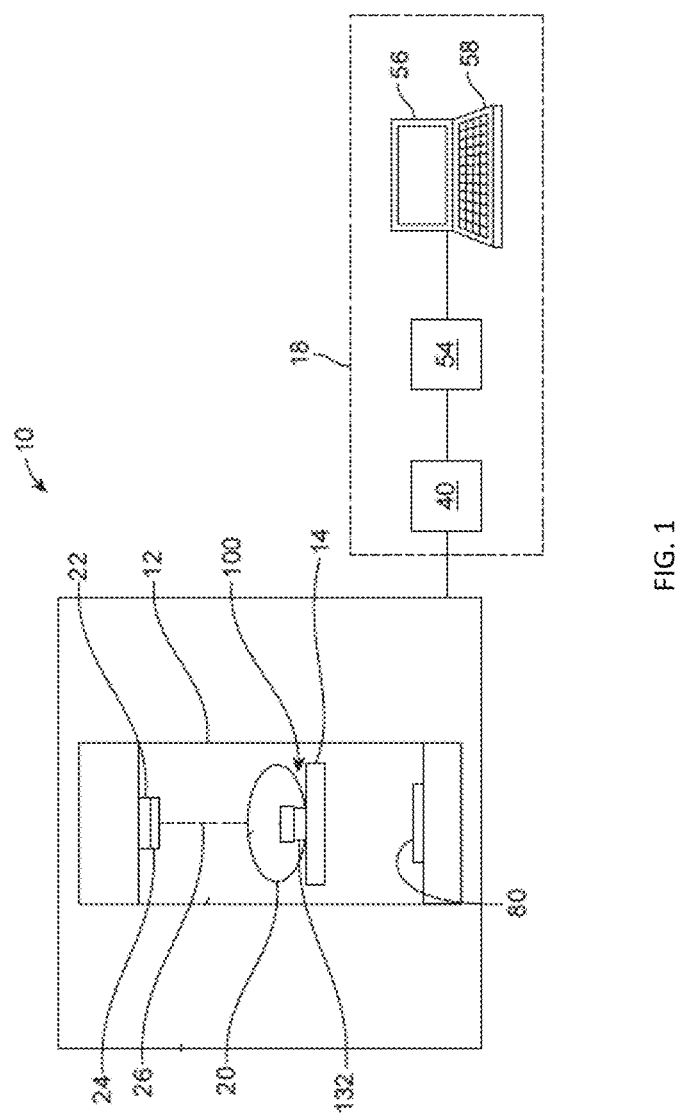
FIG. 1 illustrates a radiation treatment system configured for detecting possible collision between a moving part of a medical device and a patient during a medical procedure in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

As shown in FIG. 1, the medical system 10 also includes a camera 100. The camera 100 may be used for various purposes in a medical procedure. The camera 100 is illustrated as being mounted to the patient support by a securing mechanism 132. In other embodiments, the camera 100 may be mounted to another part of the medical system 10, or to another structure separate from the medical system 10 but is in the same room as the medical system 10. Although only one camera 100 is shown in the example, in other embodiments, the system 10 may have multiple cameras 100. For example, in other embodiments, there may be multiple cameras mounted to the system 10 and/or to other structure(s) in a medical room (such as a post, a ceiling, a floor, etc.).

Figure 2A:
FIGS. 2A-2C illustrate progression of damage to camera due to exposure to radiation.
Figure 2B:
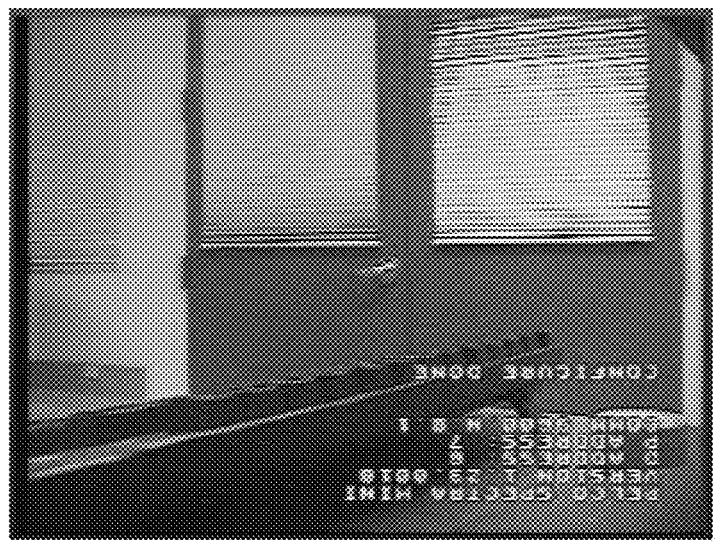
Figure 2C:
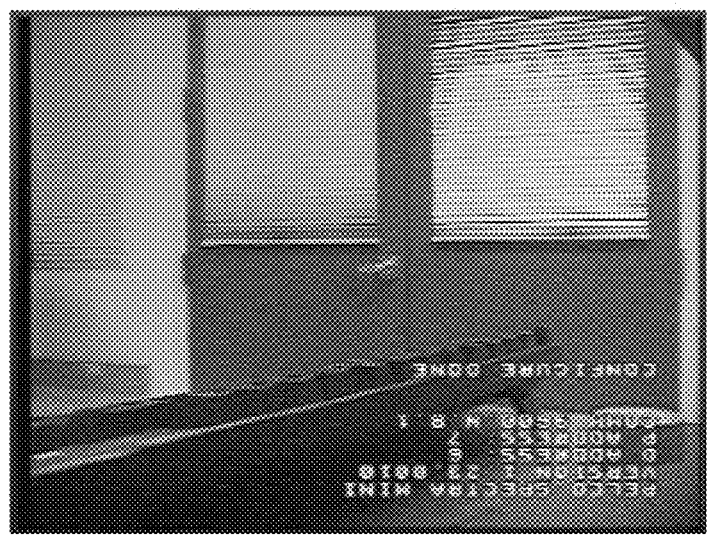

The camera 100 may be progressively damaged by radiation. Due to gradual degradation, a user may adjust to, and may tolerate, the adverse visual effect of the damage. The degradation at the camera 100 may manifest as a fixed pattern of speckle noise missing with the live image. In the case in which the camera 100 is a color video camera, such may be caused by color mask damage in a color video camera. FIGS. 2A-2C illustrate a sequence of images at increasing levels of camera degradation due to exposure to radiation. At increased levels of defect, important events occurring during a medical procedure may be missed by a therapist, who monitors the treatment room through the camera 100 on a display in the control room. For example, if the camera 100 is configured to monitor patient's movement, degradation of the camera 100 may cause a therapist and/or the processing unit (processing the images from the camera 100) to miss an important event, such as unwanted patient movements during radiation dose delivery. In another example, if the camera 100 is configured to detect possible collision between a moveable part of the system 100 and the patient, degradation of the camera 100 may cause a therapist and/or the processing unit (processing the images from the camera 100) unable to detect a possible collision between a machine part and the patient. In further example, if the camera 100 is used to track a position of a fiducial or a part of a patient in a position monitoring system for treatment and/or diagnostic purpose, degradation of the camera 100 may cause the position monitoring system to perform the tracking inaccurately.

In accordance with some embodiments, a quantitative measure of the camera defect and an automatic image analysis method that generates this quantitative measure from camera images (e.g., those from a live video stream) are provided. Such technique is advantageous because the measure may be obtained without requiring a user to run regularly scheduled tests for the camera 100. In some embodiments, the quantitative measure may be generated periodically. In other embodiments, the quantitative measure may be generated in response to a user's command. In one implementation, an image from the camera 100 may be divided into sub-regions. An algorithm may be utilized to analyze an autocorrelation function of the image in each sub-region. The goal of the algorithm is to separately quantify the local peak value in each sub-region, after autocorrelation values due to scene content is subtracted from the autocorrelation function. The algorithm also identifies the sub-regions for which this subtraction can be done with high confidence. This helps limit the noise measurement to those sub-regions only.

Figure 3:
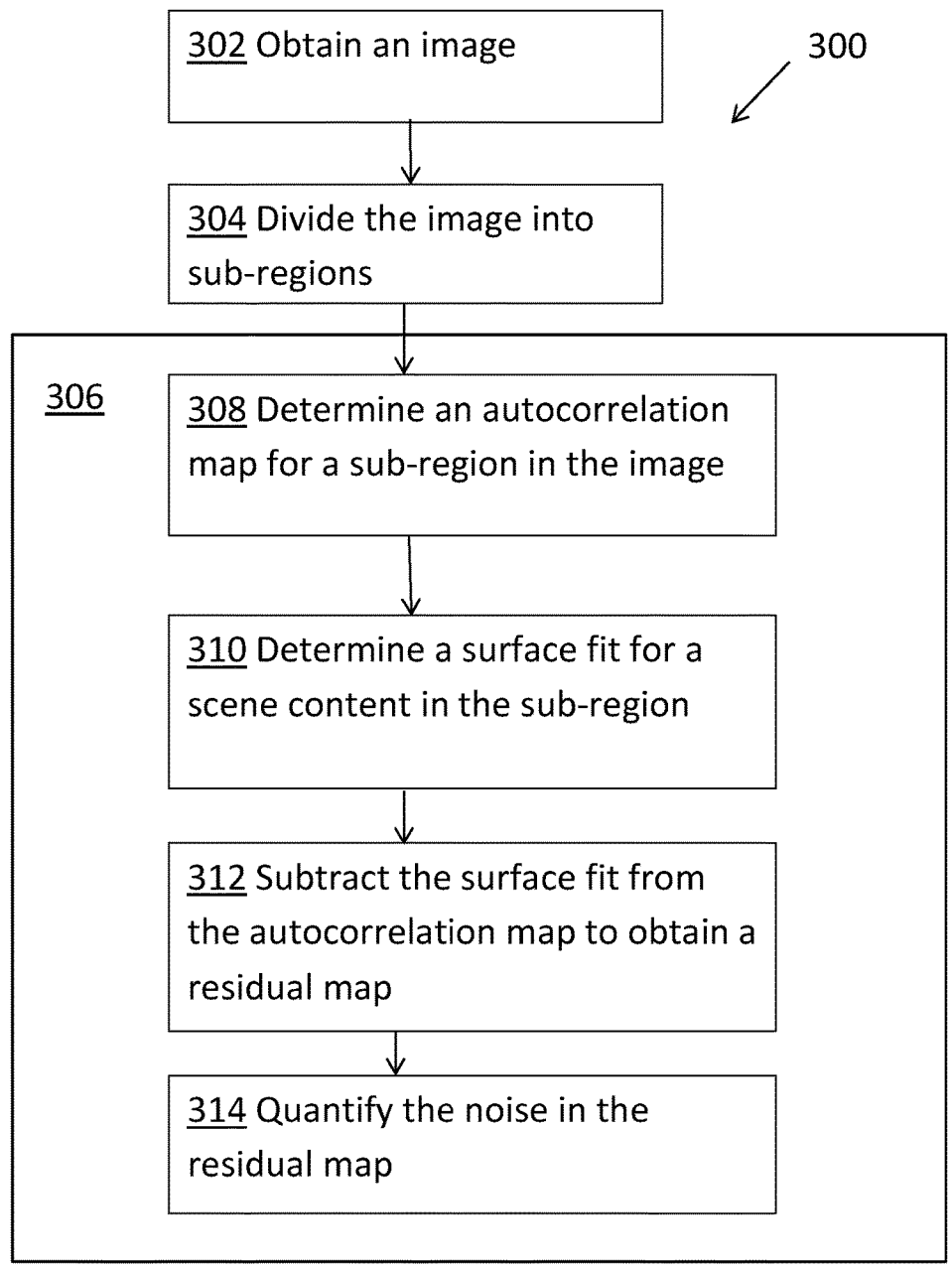
FIG. 3 illustrates a method for detecting camera defect caused by exposure to radiation in accordance with some embodiments.

FIG. 3 illustrates a method 300 for detecting camera defect caused by exposure to radiation in accordance with some embodiments. In some embodiments, the method 300 may be performed by a processing unit, which is configured to process digitized images (e.g., video frames) from the camera 100. By means of non-limiting examples, the processing unit may be the processing unit 54, or another processing unit. Also, the processing unit may be implemented using one or more processors, such as a FPGA processor, an ASIC processor, a microprocessor, a signal processor, a general purpose processor, or any of other types of processor.

First, an image from the camera 100 is obtained (item 302). In some cases, the act of obtaining the image in item 302 may be performed by a processing unit, such as the processing unit 54 or another processing unit that is communicatively coupled to the camera 100. Also, in some cases, the act of obtaining the image may be performed by the camera 100, which generates the image for transmission to a processing unit for processing. In some embodiments, the "image" may be time-average of a sequence of images obtained recursively or by block (boxcar) averaging.

Next, the image is divided into a number of sub-regions for analysis independently (item 304). In some embodiments, the image may be divided into a grid of sub-regions, each of which having a square or a rectangular shape. In other embodiments, the sub-regions may have a triangular shape, or any of other shapes. Also, in some embodiments, the sub-regions have the same shape and size. In other embodiments, one sub-regions may have a shape and/or size that is different from another sub-region. In one implementation, the division of the image into sub-regions may be performed by a processing unit, which may be the processing unit 54, or another processing unit. For example, if the image obtained from item 302 has a rectangular shape with a width of W and a height of H, and if the image is to be divided into a R=3 rolls by C=4 columns of sub-regions, then the processing unit may be configured to determine the width W' and height H' of each sub-region as W'=W/(C−1), and H'=H/(R−1). The sub-regions may or may not overlap.

In some cases, the sub-regions in an image for analysis are pre-determined. In such cases, the act of dividing the image into the sub-regions may be performed by the processing unit selecting different parts of the image corresponding with the sub-regions for analysis.

Figure 4:
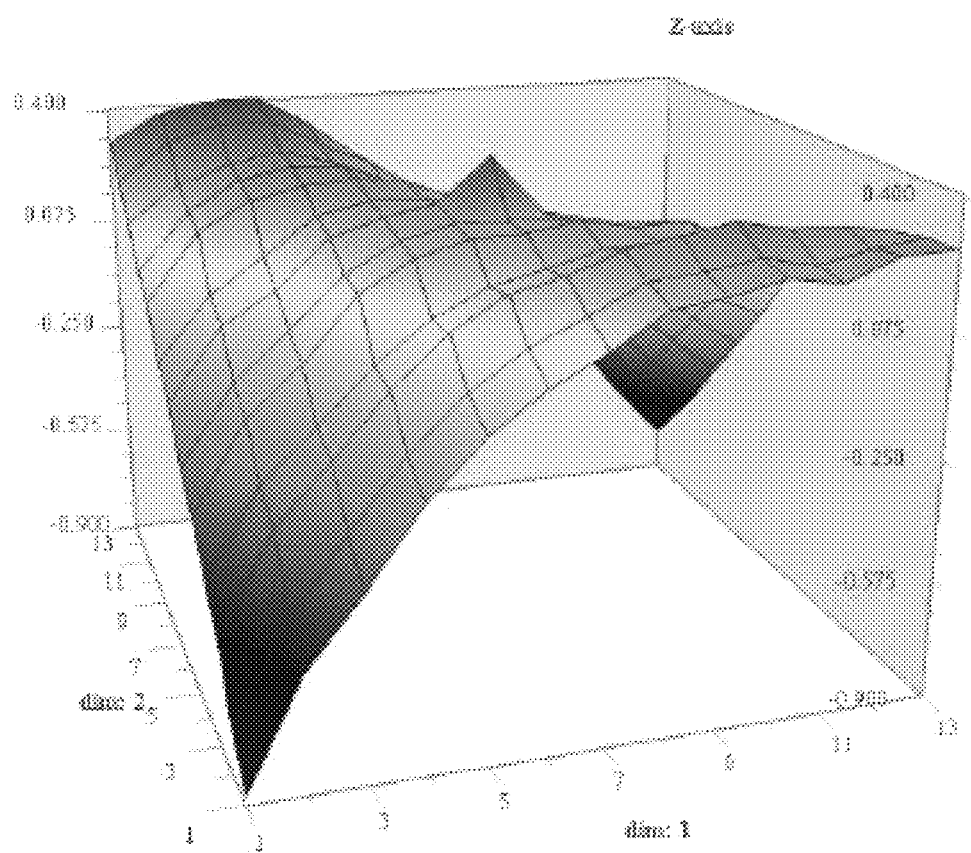
FIG. 4 illustrates an example of autocorrelation function in a sub-region.

Next, the autocorrelation function of the image in each sub-region is determined and analyzed to measure the intensity of the fixed pattern speckle noise in each sub-region (item 306). In the illustrated embodiments, item 306 includes determining an autocorrelation map for a sub-region in the image (item 308). The autocorrelation map is determined in order to 1) indicate whether in this sub-region the intensity of the speckle noise can be measured, and 2) if yes, whether speckle noise of significant intensity is present. FIG. 4 illustrates an example of autocorrelation map/function $R(x,y)$ in a sub-region. In some embodiments, $R(x,y)$ may be determined as $R(x,y)=\Sigma_{x'}\Sigma_{y'}I(x'+x,y'+y)*I(x',y')$, where the summation of the product of the image $I(x',y')$ and its shifted version $I(x'+x,y'+y)$ is over $x'$ and $y'$ within the sub-region. The purpose of this mathematical operation is to create quantitative measures that allow determination of whether the presence of speckle noise can be detected from the sub-region scene content, and whether the speckle noise intensity can be quantified. In some cases, the sub-region may be a template, which can for example comprise an N×N pixel sub-region. In the illustrated example, the value of local peak $R(0,0)$ represents the power (intensity) of the fixed pattern noise. The width of the peak, which relates to how quickly it drops off from maximum value, is proportional to the speckle noise size. Outside the area of local peak (e.g., the sidelobe regions), the variations of $R(x,y)$ is mainly influenced by the spatial frequency of the scene content in the sub-region.

Also, as shown in the illustrated embodiments, after the autocorrelation map is determined for a sub-region in the image, a surface fit for a scene content in the sub-region in the image is then determined (item 310). The surface fit is for accounting for local scene content. Various techniques may be used to account for the local scene content. In one technique, a planar fit may be performed by the processing unit to fit to the sidelobe regions of the autocorrelation function $R(x,y)$. For example, this may be done by excluding a region around (0,0) in the correlation map. The size of the excluded region may be determined based on the knowledge of the noise speckle size. The planar fit is made to the remaining points of the correlation map after this exclusion. One method of planar fit is to estimate the plane coefficients which minimize the residual correlation map values after subtracting the fitted plane. For example the RMS (root mean squared) value of the residual values may be minimized.

In other embodiments, instead of a planar fit, the processing unit may determine a higher order polynomial surface, and may use it to subtract the scene content contributing to the autocorrelation map. Accordingly, the surface fit performed by the processing unit may be planar, or non-planar.

Next, the processing unit subtracts the plane of the planar fit from the autocorrelation function $R(x,y)$ to obtain a residual map $R'(x,y)$ (item 312).

After the surface fit (i.e., representing autocorrelation values due to scene content) is subtracted from the autocorrelation function in a sub-region, the processing unit then quantifies the local peak for that sub-region (item 314). In some cases, the processing unit quantifies the local peak by determining a magnitude of the local peak representing noise.

The processing unit is configured to perform the surface fit determination (item 310), surface fit subtraction (item 312), and local peak quantification (item 314) for each of the sub-regions in the image. For example, in one implementation, the processing unit may include a surface fit module configured to determine the surface fit that corresponds with the scene content. The processing unit may also include a surface fit subtraction module configured to receive the surface fit and the autocorrelation function $R(x,y)$ as inputs, and output $R'(x,y)$, which is obtained by subtracting the surface fit from $R(x,y)$. The processing unit may also include a local peak quantification module configured to quantify the local peak.

In some cases, if the quantified noise (e.g., a magnitude of the noise) in a sub-region is less than a threshold, then the peak quantification module may classify that sub-region as having "low" noise. On the other hand, if the quantified noise in the sub-region is more than a threshold, then the peak quantification module may classify that sub-region as having "high" noise.

Figure 5A:
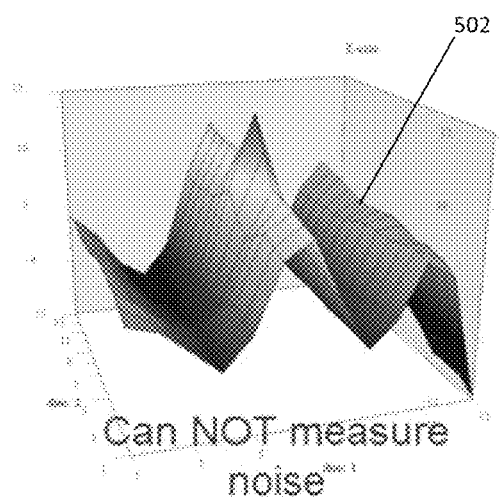
FIGS. 5A-5B illustrate examples of autocorrelation map after planar fit subtraction for a high scene content, and a bland scene content, respectively.
Figure 5B:
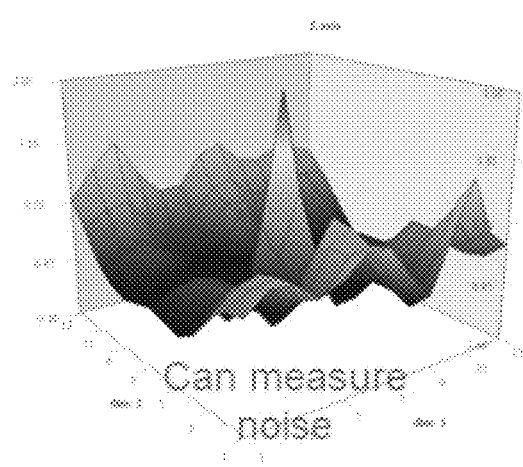

In some embodiments, the processing unit also identifies the sub-regions for which the noise quantification can be done with high confidence. This helps limit the noise measurement to those sub-regions only. In some cases, after the surface fit subtraction, if there is excessive residual sidelobe, then the noise in that sub-region cannot be measured accurately. FIGS. 5A-5B illustrate examples of autocorrelation map after surface fit subtraction for a high scene content, and a bland scene content, respectively. As shown in FIG. 5A, because the sub-region has high scene content, after determining the surface fit for that sub-region, and after subtracting the surface fit from the autocorrelation map for that sub-region, the residual map $R'(x,y)$ may have excessive residual sidelobe(s) 502. In such cases, the quantified peak may not be determined with high confidence. On the other hand, as shown in FIG. 5B, if the sub-region has bland scene (low scene content), after determining the surface fit for that sub-region, and after subtracting the surface fit from the autocorrelation map for that sub-region, the residual map R'(x,y) may not have any excessive residual sidelobe. In such cases, the quantified peak may be determined with high confidence.

In one implementation, the processing unit may include a confidence level module configured to determine a confidence level associated with each sub-region. In particular, the confidence level is configured to determine, for each of the sub-regions in the image, whether there is excessive residual sidelobe after the surface fit subtraction. If a sub-region has excessive residual sidelobe, then this may then be used to indicate that the peak for that sub-region cannot be determined with confidence. If the contribution of scene content is successfully subtracted from the autocorrelation map R(x,y), then the remaining sidelobe standard deviation should be mainly due to speckle noise. Under some approximating assumptions, the standard deviation of a residual sidelobe (obtained after the surface fit subtraction) should be less than the peak value by a factor of M, where M is proportional to N, and where an N×N template is used to calculate the autocorrelation surface map. Thus, M is proportional to the square root of the total number of pixels in the template. A completely "bland" scene results in perfect surface fit wherein the noise-only threshold of PSR (peak-to-sidelobe ratio) may be used. In some cases, a smaller PSR threshold may be used, thereby allowing for some slow intensity variation due to scene content.

The resulting residual map R'(x,y) may then be analyzed by the processing unit for determining peak-to-sidelobe ratio (PSR). In some cases, the sidelobe standard deviation is simply the standard deviation of the residuals after planar fit subtraction. Also, the peak may be R(0,0) (after planar fit subtraction), which also determines the noise level. If the contribution of the scene content is successfully subtracted, then the remaining sidelobe standard deviation should be mainly due to the speckle noise (resulted from the damage to the camera 100).

Figure 6:
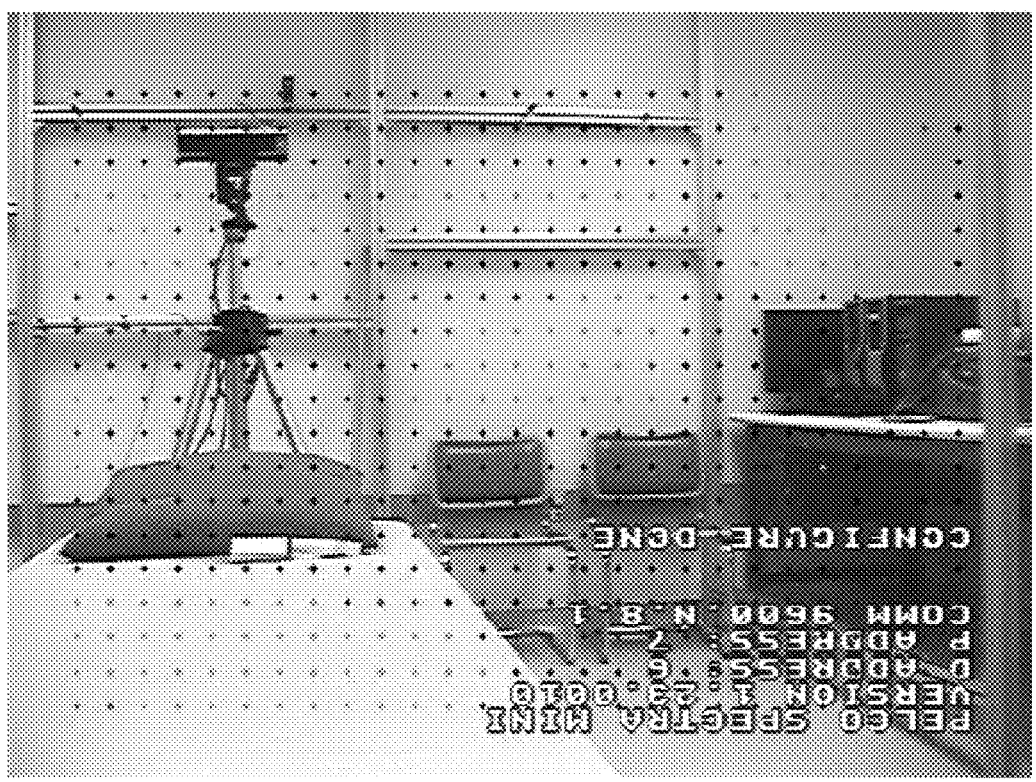
FIG. 6 illustrates an example of a result obtained by using the method of FIG. 3.

In some embodiments, information regarding the determined noise may be output by the processing unit for display in a screen. FIG. 6 illustrates an example of a result obtained by using the method of FIG. 3. As shown in the figure, the processing unit generates multiple indicators that are displayed over the image. Each indicator is in a form of a dot, and is at a location that corresponds with a position of the corresponding sub-region in the image. In the illustrated example, the blue dots indicate the sub-regions where the noise could not be measured because of excessive residual sidelobe after the surface fit subtraction. The green dots indicate sub-regions where noise could be measured (because there is no excessive residual sidelobe after the surface fit subtraction), and the noise was less than a threshold (e.g., 2 counts standard deviation out of 256 counts for an 8-bit digitized image). The red dots show the sub-regions where noise could be measured (because there is no excessive residual sidelobe after the surface fit subtraction), and the noise RMS was larger than the threshold (e.g., 2).

Also, in some embodiments, each indicator in the screen represents information regarding a noise in a sub-region of the image, and may be generated by the processing unit. In particular, after the processing unit obtains an image, the processing unit may then determines a first autocorrelation map for a first sub-region in the image; determine, using the surface fit module, a first surface fit for first scene content in the first sub-region; subtract, using the subtraction module, the first surface fit from the first autocorrelation map for the first sub-region in the image to obtain a first residual map; and quantify, using the peak quantification module, a first noise in the first residual map. The quantified first noise may then be represented by a first indicator in the screen. The processing unit may also determine a second autocorrelation map for a second sub-region in the image; determine a second surface fit for second scene content in the second sub-region; subtract the second surface fit from the second autocorrelation map for the second sub-region in the image to obtain a second residual map; and quantify a second noise in the second residual map. The quantified second noise may then be represented by a second indicator in the screen.

In the above example, the information regarding the noise is presented as an indicator that is in a form of a dot. In other embodiments, the information regarding the noise may be presented in other forms. For example, in other embodiments, the information regarding the noise may be presented in the form of texts, such as a number indicating the actual level of the determined noise in each of the sub-regions in the image. Also, the information may also include a level of confidence associated with the determined noise in each of the sub-regions in the image. In some embodiments, the result may be written to a log file (e.g., a radiation machine performance check log file) which is updated at specified time intervals.

In some embodiments, a processing unit (e.g., the processing unit 54 or another processing unit) may be configured to determine a temporal average of N number of image frames.

Figure 7:
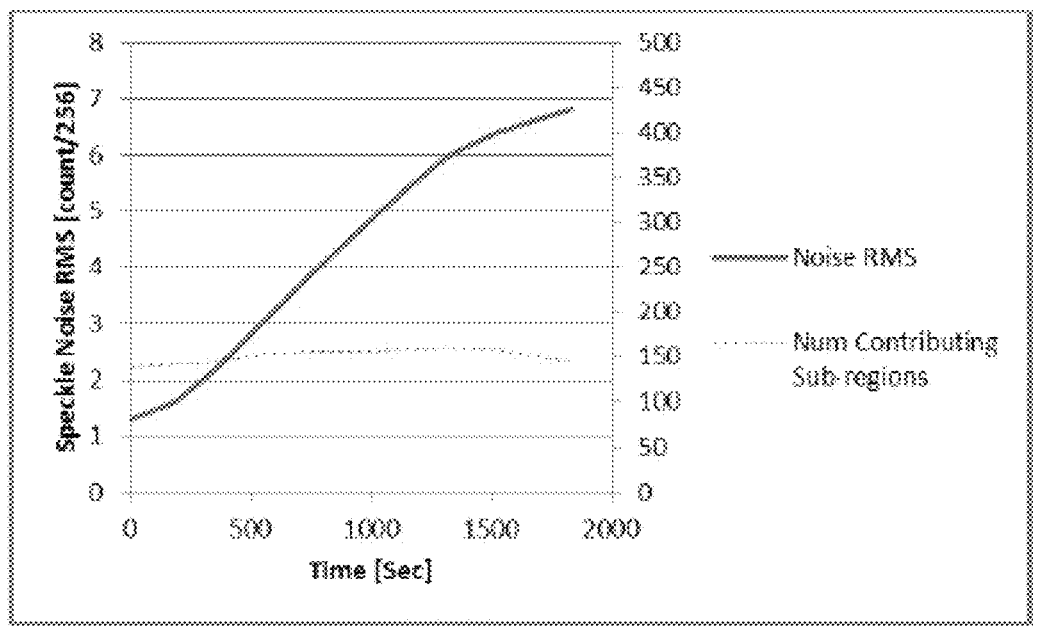
FIG. 7 illustrates noise as a function of degradation time for a camera exposed to radiation.
Figure 8:
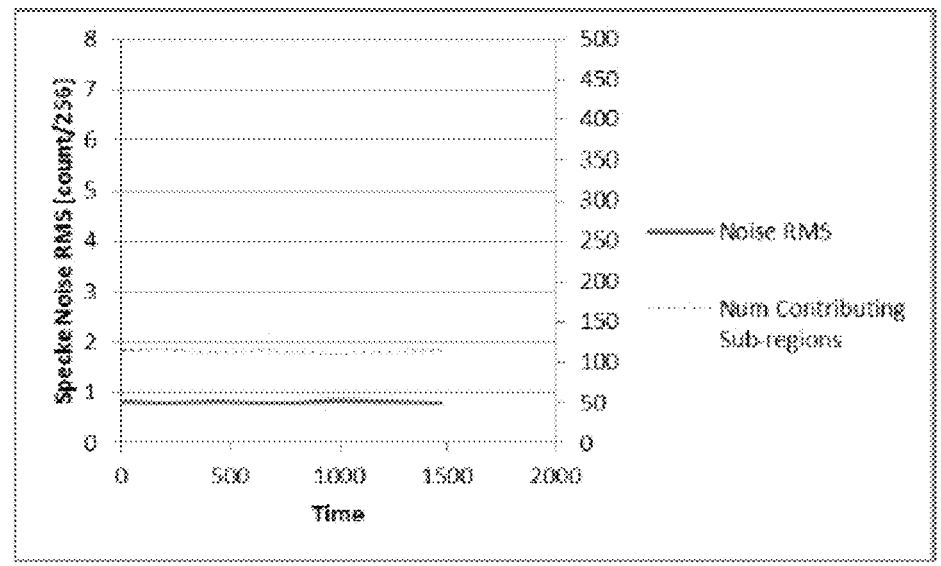
FIG. 8 illustrates noise as a function of degradation time for a camera not exposed to radiation.

In some cases, the determined noise as a function of degradation time may be provided for a user. FIG. 7 illustrates an example of noise as a function of degradation time for a camera exposed to radiation. In particular, the noise is represented as speckle noise RMS values in the y-axis (e.g., counts/256 for a gray scale image). The x-axis represents degradation time. The figure also shows the number of sub-regions where noise can be measured with high confidence. As shown in the figure, when a camera is exposed to radiation, the noise RMS increases over time. FIG. 8 illustrates noise as a function of degradation time for a camera not exposed to radiation. This figure also shows the number of sub-regions where noise can be measured with high confidence. As shown in the figure, when a camera is not exposed to radiation, the noise RMS stays relatively constant over time.

As shown in FIGS. 7 and 8, the relatively constant number of sub-regions (from which noise measurement may be determined with high confidence) over time may serve as a validation of the noise measurement.

As shown in FIGS. 7 and 8, the processing unit may be configured to determine multiple information regarding a noise in a sub-region over time, to thereby determine how the degradation of the camera occurs over time. In particular, the processing unit may obtain a first image at a first time. The processing unit may then determine a first autocorrelation map for a first sub-region in the first image; determine, using the surface fit module, a first surface fit for first scene content in the first sub-region; subtract, using the subtraction module, the first surface fit from the first autocorrelation map for the first sub-region in the first image to obtain a first residual map; and quantify, using the peak quantification module, a first noise in the first residual map. Later, at a different time, the processing unit may obtain an additional (second) image. The processing unit may then determine a second autocorrelation map for a second sub-region in the additional image; determine a second surface fit for second scene content in the second sub-region; subtracting the second surface fit from the second autocorrelation map for the second sub-region in the image to obtain a second residual map; and quantifying a second noise in the second residual map. Thus, the first image and the additional image are obtained at different respective times. Also, a position of the first sub-region with respect to the image is a same as a position of the second sub-region with respect to the additional image. After the quantified first noise and the quantified second noise is obtained, they may be output by the processing unit for presentation as a function of time.

As shown in the above embodiments, the system and method described herein are advantageous because they allow for in-service detection and quantification of fixed pattern speckle noise in video camera.

Although the above embodiments have been described with reference to detecting damage and/or deterioration in camera caused by radiation, in other embodiments, the technique and device described herein may be employed to test any camera (e.g., camera for medical use, or camera for non-medical use), which may or may not be exposed to any radiation. For examples, in other embodiments, the technique and device described herein may be used to test and/or monitor cameras in nuclear research and power plant facilities.

Processing System Architecture

Figure 9:
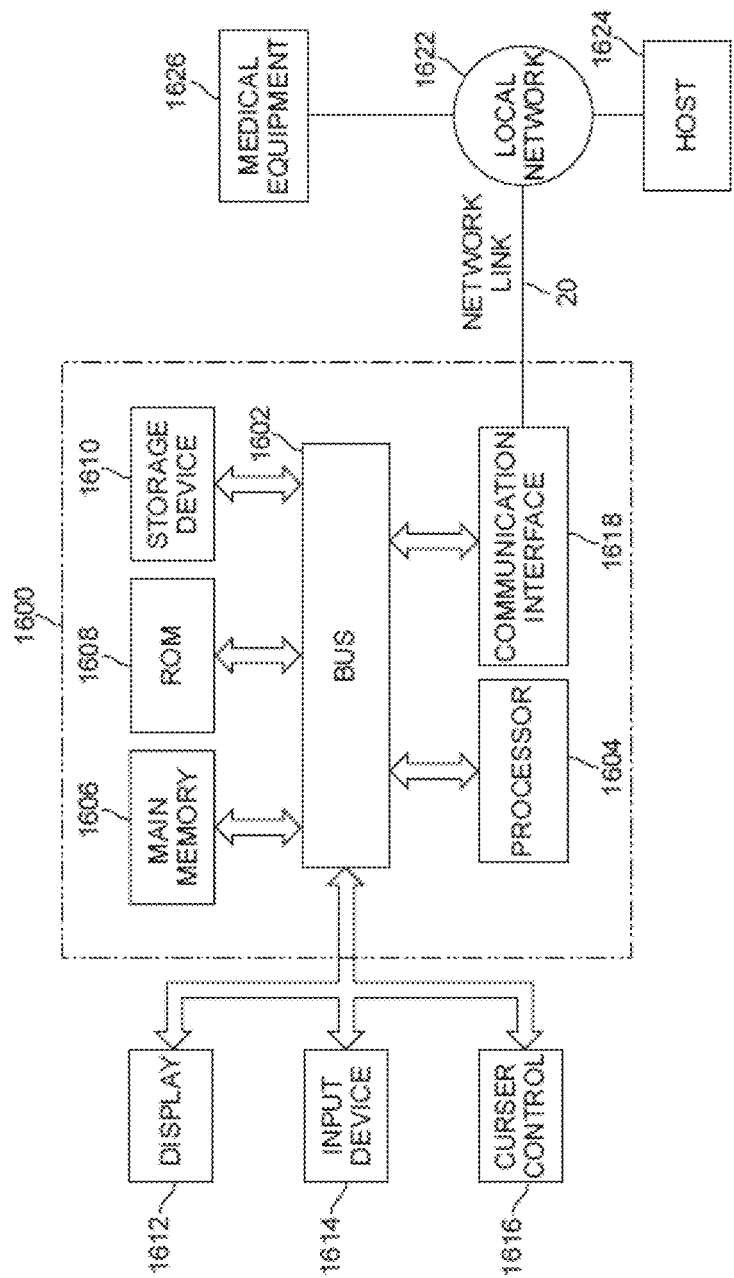
FIG. 9 illustrates a specialized processing system with which embodiments described herein may be implemented.

FIG. 9 is a block diagram illustrating an embodiment of a specialized processing system 1600 that can be used to implement various embodiments described herein. For example, the processing system 1600 may be configured to implement the method of FIG. 3 in accordance with some embodiments. Also, in some embodiments, the processing system 1600 may be used to implement the processing unit 54 of FIG. 1. The processing system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The processing system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processing system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processing system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processing system 1600 can be used to perform various functions described herein. According to some embodiments, such use is provided by processing system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method of detecting camera defect, comprising:
    obtaining an image by a processing unit, the processing unit having a surface fit module, a subtraction module, and a peak quantification module, wherein the image is generated using a camera;
    determining a first autocorrelation map for a first sub-region in the image;
    determining, using the surface fit module, a first surface fit for first scene content in the first sub-region;
    subtracting, using the subtraction module, the first surface fit from the first autocorrelation map for the first sub-region in the image to obtain a first residual map;
    quantifying, using the peak quantification module, a first noise in the first residual map; and
    providing an indication based on a result from the act of quantifying the first noise to indicate whether the camera is defective or not.

2. The method of claim 1, wherein the act of determining the surface fit comprises determining a planar surface that represents the first scene content.

3. The method of claim 1, wherein the act of determining the surface fit comprises determining a non-planar surface that represents the first scene content.

4. The method of claim 1, wherein the act of quantifying the first noise comprises determining whether a magnitude of the first noise exceeds a threshold or not.

5. The method of claim 1, further comprising determining a level of confidence associated with the quantified first noise.

6. The method of claim 5, wherein the act of determining the level of confidence comprises determining a standard deviation associated with a residual sidelobe in the first residual map.

7. The method of claim 1, further comprising displaying the image in a screen, and displaying an indicator representing the quantified first noise in the screen.

8. The method of claim 7, wherein the indicator has a first color if the quantified first noise is above a threshold, and a second color if the quantified first noise is below the threshold.

9. The method of claim 7, wherein:
    the indicator has a first color if the quantified first noise is above a threshold, and the quantified first noise is determined with confidence,
    the indicator has a second color if the quantified first noise is below the threshold, and the quantified first noise is determined with confidence, and
    the indicator has a third color if the quantified first noise cannot be determined with confidence.

10. The method of claim 7, wherein the indicator is displayed over the image, and is at a location that corresponds with a position of the sub-region in the image.

11. The method of claim 7, wherein the indicator comprises a dot.

12. The method of claim 1, further comprising:
    determining a second autocorrelation map for a second sub-region in the image;
    determining a second surface fit for second scene content in the second sub-region;
    subtracting the second surface fit from the second autocorrelation map for the second sub-region in the image to obtain a second residual map; and
    quantifying a second noise in the second residual map.

13. The method of claim 1, further comprising:
    obtaining an additional image;
    determining a second autocorrelation map for a second sub-region in the additional image;
    determining a second surface fit for second scene content in the second sub-region;
    subtracting the second surface fit from the second autocorrelation map for the second sub-region in the image to obtain a second residual map; and
    quantifying a second noise in the second residual map;
    wherein the first image and the additional image are obtained at different respective times; and
    wherein a position of the first sub-region with respect to the image is a same as a position of the second sub-region with respect to the additional image.

14. The method of claim 13, further comprising presenting the quantified first noise and the quantified second noise as a function of time.

15. An apparatus for detecting camera defect, comprising:
    a processing unit having a surface fit module, a subtraction module, and a peak quantification module;
    wherein the processing unit is configured to obtain an image generated using a camera, and determining a first autocorrelation map for a first sub-region in the image;
    wherein the surface fit module is configured to determine a first surface fit for first scene content in the first sub-region;
    wherein the subtraction module is configured to subtract the first surface fit from the first autocorrelation map for the first sub-region in the image to obtain a first residual map;
    wherein the peak quantification module is configured to quantify a first noise in the first residual map; and
    wherein the processing unit also comprises an indication generator for providing an indication based on a result from the quantified first noise to indicate whether the camera is defective or not.

16. The apparatus of claim 15, wherein the surface fit module is configured to determine the surface fit by determining a planar surface that represents the first scene content.

17. The apparatus of claim 15, wherein the surface fit module is configured to determine the surface fit by determining a non-planar surface that represents the first scene content.

18. The apparatus of claim 15, wherein the peak quantification module is configured to quantify the first noise by determining whether a magnitude of the first noise exceeds a threshold or not.

19. The apparatus of claim 15, further comprising a confidence level module configured to determine a level of confidence associated with the quantified first noise.

20. The apparatus of claim 19, wherein the confidence level module is configured to determine the level of confidence by determining a standard deviation associated with a residual sidelobe in the first residual map.

21. The apparatus of claim 15, further comprising a screen for displaying the image, and for displaying an indicator representing the quantified first noise.

22. The apparatus of claim 21, wherein the indicator has a first color if the quantified first noise is above a threshold, and a second color if the quantified first noise is below the threshold.

23. The apparatus of claim 21, wherein:
the indicator has a first color if the quantified first noise is above a threshold, and the quantified first noise is determined with confidence,
the indicator has a second color if the quantified first noise is below the threshold, and the quantified first noise is determined with confidence, and
the indicator has a third color if the quantified first noise cannot be determined with confidence.

24. The apparatus of claim 21, wherein the screen is configured to display the indicator over the image at a location that corresponds with a position of the sub-region in the image.

25. The apparatus of claim 21, wherein the indicator comprises a dot.

26. The apparatus of claim 15, wherein the processing unit is configured to determine a second autocorrelation map for a second sub-region in the image;
wherein the surface fit module is configured to determine a second surface fit for second scene content in the second sub-region;
wherein the subtraction module is configured to subtract the second surface fit from the second autocorrelation map for the second sub-region in the image to obtain a second residual map; and
wherein the peak quantification module is configured to quantify a second noise in the second residual map.

27. The apparatus of claim 15, wherein the processing unit is configured to obtain an additional image, and determine a second autocorrelation map for a second sub-region in the additional image;
wherein the surface module is configured to determine a second surface fit for second scene content in the second sub-region;
wherein the subtraction module is configured to subtract the second surface fit from the second autocorrelation map for the second sub-region in the image to obtain a second residual map; and
wherein the peak quantification module is configured to quantify a second noise in the second residual map;
wherein the first image and the additional image are obtained at different respective times; and
wherein a position of the first sub-region with respect to the image is a same as a position of the second sub-region with respect to the additional image.

28. The apparatus of claim 27, further comprising a screen for presenting the quantified first noise and the quantified second noise as a function of time.

29. A processor-program product having a set of instruction stored in a processor-readable non-transitory medium, an execution of which by a processing unit causes a method of detecting camera defect to be performed, the method comprising:
obtaining an image generated using a camera;
determining a first autocorrelation map for a first sub-region in the image;
determining, using a surface fit module, a first surface fit for first scene content in the first sub-region;
subtracting, using a subtraction module, the first surface fit from the first autocorrelation map for the first sub-region in the image to obtain a first residual map;
quantifying, using a peak quantification module, a first noise in the first residual map; and
providing an indication based on a result from the act of quantifying the first noise to indicate whether the camera is defective or not.

* * * * *